US 7,011,970 B2

(12) United States Patent
Kim et al.

(10) Patent No.: US 7,011,970 B2
(45) Date of Patent: Mar. 14, 2006

(54) AUTOMATIC BIO-MANIPULATION FACTORY SYSTEM FOR MANIPULATING A SINGLE CELL

(75) Inventors: Byung-Kyu Kim, Seoul (KR); Jung-Yul Park, Seoul (KR); Deok-Ho Kim, Seoul (KR); Jong-Oh Park, Seoul (KR)

(73) Assignee: Korean Institution of Science and Technology, Seoul (KR)

( * ) Notice: Subject to any disclaimer, the term of this patent is extended or adjusted under 35 U.S.C. 154(b) by 369 days.

(21) Appl. No.: 10/400,290

(22) Filed: Mar. 25, 2003

(65) Prior Publication Data

US 2004/0092002 A1 May 13, 2004

(30) Foreign Application Priority Data

Nov. 12, 2002 (KR) ................................ 10-2002-0070114

(51) Int. Cl.
*A01N 1/00* (2006.01)

(52) U.S. Cl. ................................ 435/284.1; 435/285.1; 435/285.2; 435/288.6; 435/288.7; 204/451; 204/454; 204/547; 359/369; 359/376; 384/133; 600/33

(58) Field of Classification Search .............. 435/284.1, 435/285.1, 285.2, 286.2, 288.6, 288.7; 204/451, 204/454, 547; 359/369, 376; 384/133; 600/33
See application file for complete search history.

(56) References Cited

U.S. PATENT DOCUMENTS

| | | | | |
|---|---|---|---|---|
| 5,114,854 A | * | 5/1992 | Bertholdt ..................... | 435/30 |
| 6,193,647 B1 | * | 2/2001 | Beebe et al. ................. | 600/33 |
| 6,468,784 B1 | * | 10/2002 | Takeshita et al. ........ | 435/287.1 |
| 6,593,129 B1 | * | 7/2003 | Takeshita et al. ........ | 435/285.1 |
| 2002/0039280 A1 | | 4/2002 | O'Connor et al. ........ | 361/690 |

OTHER PUBLICATIONS

Patent Abstracts Of Japan, JP 11–347971, Application No. 10 162011 (Tokai Rika Co Ltd), abstract.
Fumihito Arai, et al, "Three–Dimensional Bio–Micromanipulation under the Microscope", Proceedings of the 2001 IEEE, International Conference on Robotics & Automation, Seoul, Korea, pp. 604–609.
Fumihoto Arai, Toru Kasugai, and Toshio Fukuda, "3D Position and Orientation Control Method of Micro Object by Dielectrophoresis", 1998 International Symposium on Micromechatronics and Human Science, pp 149–154.
Sun Yu, Bradley J. Nelson, Microrobotic Cell Injection, Proceedings of the 2001 IEEE, International Conference on Robotics & Automation, Seoul, Korea, pp. 620–625.

(Continued)

*Primary Examiner*—David Redding
(74) *Attorney, Agent, or Firm*—Armstrong, Kratz, Quintos, Hanson & Brooks, LLP

(57) ABSTRACT

This new automatic bio-manipulation factory system for manipulating a single cell comprises: a bio-MEMS that transports, separates, and extracts a single cell for manipulation from a plurality of cells, controls the rotation-orientation of the extracted cell automatically, and enables the extracted cell to maintain a certain temperature; and a micro manipulation system that obtains vision information and manipulation information about the extracted single cell and the manipulation tool, provides such information to operator, manipulates the extracted single cell by transmitting the rotation-orientation feedback information and the cell manipulation order of the operator to the bio-MEMS, and manipulates the manipulation tool by transmitting the tool manipulation order of the operator to the manipulation tool. The conventional manual and individualized single cell manipulation can be automated and processed collectively by systematically combining the bio-MEMS with the micro manipulation system.

13 Claims, 9 Drawing Sheets

OTHER PUBLICATIONS

Xudong Li, Guanghua Zong and Shusheng Bi, "Development of Global Vision System for Biological Automatic Micro–Manipulation System", Proceedings of the 2001 IEEE, International Conference on Robotics & Automation, Seoul, Korea, pp. 127–132.

Ian K. Glasgow et al, "Handling Individual Mammalian Embryos Using Microfluidics", IEEE Transactions on Biomedical Engineering, vol. 48, No. 5, May 2001.

H. C. Zeringue et al, "Micro Fluidic Single Embryo Culture Systems in PDMS", Proceedings of the First Joint BMES/EMBS Conference Serving Humanity, Advancing Technology Oct. 13–16, 1999, Atlanta, Ga, USA, p. 851.

Edwin W. H. Jager et al, "The Cell Clinic; Closable Microvials for Single Cell Studies", Biomedical Microdevices 4:3, 177–187, 2002.

* cited by examiner

AUTOMATIC BIO-MANIPULATION FACTORY SYSTEM FOR MANIPULATING A SINGLE CELL

BACKGROUND OF THE INVENTION

1. Field of the Invention

The present invention relates to a batched and automatic bio-manipulation factory system for manipulating a single cell and, more particularly, to an automatic bio-manipulation factory system for manipulating a single cell, which transports, separates and extracts a single cell to be subjected to manipulation from a plurality of cells, controls the rotation-orientation of the extracted single cell, and precisely manipulates the extracted cell by a biomimic smart micro pipette using a vision unit and a haptic unit.

2. Description of the Related Art

In general, in order to manipulate a cell through methods such as gene alteration, DNA injection, cell fusion and so forth, it is essential to precisely manipulate the relevant cell at the exact position using a micro manipulation system.

However, the bio-manipulation factory systems of the related art such as the ICSI (Intracytoplasmic Sperm Injection) system which has been used for the IVF (in vitro fertilization) operation show great variance in the efficiency depending on the skill of the operator. Thus, there is a problem in the conventional bio-manipulation systems that an operator can manipulate a cell appropriately only if he or she has received cell manipulation training for a long time. This problem originates from the difficulty in determining the speed and strength with which to manipulate a cell because only the vision information is available for cell manipulation.

Further, the bio-manipulation factory system using the laser to separate a single cell from a plurality of cells, that is used ordinarily for manipulation of a specific single cell extracted out of a plurality of cells of animals (e.g., fertilized eggs of a mouse), is also problematic because of its high price.

On the other hand, because the technology in the related art concerning the bio-MEMS (Micro-Electro Mechanical System) mainly focuses on the bio-analysis function on a plurality of cells and the technology in the related art concerning the micro manipulation system only focuses on manipulating a single cell, the extraction and rotation of a single cell is mainly accomplished manually in the related art. Thus, it is very difficult to conduct the precise manipulation of cells using the technologies in the related art.

Moreover, for the control of the rotation-orientation of a cell, which is essential for the single cell manipulation, the rotation-orientation of a cell needs to be such that chromosomes and polar bodies may be manipulated with a micro pipette at the time of nucleus alteration. However, in the related art, because the cell is rotated through manual operation of a micro pipette, the cell may be damaged during the manipulation and, further, it is difficult to precisely control the rotation-orientation of the cell.

SUMMARY OF THE INVENTION

The object of the present invention is, in order to solve problems mentioned above, to implement a bio-MEMS using capillary electrophoresis, dielectrophoresis and the conductive polymer, which may transport, separate and extract a single cell for manipulation from a plurality of cells and which may control the rotation-orientation of the extracted cell by a vision unit at the time of manipulating the cell.

It is another object of the present invention to improve the precision degree of the cell manipulation and to enable a non-expert to conduct the precise cell manipulation by systematically combining the bio-MEMS with a micro manipulation system including a vision unit, a haptic unit, a control unit, a biomimic smart pipette and a holding pipette.

In order to solve the above-mentioned problems existing in the related art, the automatic bio-manipulation factory system for manipulating a single cell according to the present invention comprises: a bio-MEMS that transports, separates, and extracts a single cell for manipulation from a plurality of cells, controls the rotation-orientation of the extracted cell automatically, and enables the extracted cell to maintain a certain temperature; and a micro manipulation system that obtains vision information and manipulation information about the extracted single cell and the manipulation tool, provides such information to operator, manipulates the extracted single cell by transmitting the rotation-orientation feedback information and the cell manipulation order of the operator to the bio-MEMS, and manipulates the manipulation tool by transmitting the tool manipulation order of the operator to the manipulation tool.

The bio-MEMS comprises: an input unit that stores a plurality of inputted cells and transports the plurality of cells in a line by controlling the size of the cell transportation channel through the use of the capillary electrophoresis caused by application of the transportation voltage and the focus voltage; an injection unit including an injection port that separates cells for manipulation from the plurality of cells transported in a line by applying the separation voltage; an extraction unit that extracts one of the cells separated for manipulation by applying the extraction voltage and manipulates the rotation-orientation of the cell by applying the rotation-orientation voltage; and a drain unit that absorbs the rest of the cells other than the cells separated for manipulation.

The input unit comprises: a first focus port that transports the first flow by applying the first focus voltage; a second focus port that transports the second flow by applying the second focus voltage which is the same as the first focus voltage; and an input cell storage port that stores a plurality of the inputted cells and transports the plurality of cells though the third flow to the cell transportation channel formed between the first flow and the second flow by applying the transportation voltage. Preferably, the size of the cell transportation channel is such that the plurality of cells may pass in one line.

The extraction unit comprises: a conductive polymer that extracts only one out of the cells separated for manipulation; an extraction controller that controls the cell extraction of the conductive polymer; and a cell manipulator that controls temperature of the extracted single cell and rotation-orientation of the extracted single cell by applying the rotation-orientation voltage. Preferably, the conductive polymer is made of poly pyrrole.

The cell manipulator comprises: an extraction port that absorbs the single cell extracted for manipulation by applying the extraction voltage; a heater, included in the extraction port, that controls the temperature of the extracted single cell; a temperature controller for the heater; rotation-orientation electrodes, located around the extraction port, that manipulate the rotation-orientation of the extracted single cell using the dielectrophoresis by applying the rotation-orientation voltage; and a rotation-orientation controller that receives rotation-orientation feedback information and cell manipulation order of the operator and then controls the rotation-orientation electrodes' manipulation of the cell rotation-orientation.

Preferably, the rotation-orientation controller controls automatically the rotation-orientation of the extracted single cell so that it may be located at the operator's desired rotation-orientation or at the previously inputted rotation-orientation according to the rotation-orientation feedback information.

The drain unit comprises: a third focus port that absorbs the first flow by applying the third focus voltage; a fourth focus port that absorbs the second flow by applying the fourth focus voltage which is the same as the third focus voltage; and a drain cell storage port that stores the rest of the cells other than the cell separated for manipulation through the third flow from the cell transportation channel formed between the first flow and the second flow, by applying the drain voltage.

The micro manipulation system comprises: a vision unit that monitors the extracted single cell and the manipulation tool by using a microscope in real-time and then outputs vision information and rotation-orientation feedback information; a haptic unit, equipped with a force sensor measuring changes in the cell manipulation force, that collects and outputs information on the extracted single cell and the manipulation tool and that receives tool manipulation order of the operator and then outputs it to the manipulation tool; a control unit that provides the operator with the outputted vision information and manipulation information, outputs the cell manipulation order of the operator to an extraction unit, and outputs the tool manipulation order of the operator to the haptic unit; a biomimic smart micro pipette that senses the cell manipulation force, outputs trigger information, and manipulates the cell according to the tool manipulation order of the operator; and a holding pipette that controls the rotation-orientation of a cell at the time of manipulating the cell and then fixes the orientation of the cell according to the tool manipulation order of the operator which has been transmitted from the control unit. Preferably, the microscope, which has the fluorescence function, is a confocal microscope or an optical microscope.

The vision unit outputs the rotation-orientation feedback information based on the vision information acquired by the microscope's monitoring and controls automatically the rotation-orientation of the extracted single cell so that it may be located at the operator's desired rotation-orientation or at the previously inputted rotation-orientation.

The biomimic smart micro pipette comprises: a physical force sensor that senses manipulation force at the time of manipulating the cell; a trigger sensor that outputs trigger information at the time of contacting the cell; a pointed tip that vents chemical material which may melt zonapellucida of the cell when a trigger signal is generated by the contact of the cell; an injection mechanism part that enables accurate manipulation while imposing the minimum invasion on the cell at the time of manipulating the cell by using the rotation and impact drive mechanism; and an injector that enables the injection of chemical material or bio-material necessary for the cell manipulation. Preferably, the trigger sensor is either an electric trigger sensor that outputs the trigger signal by the change in the potential difference of the cell surface or a bio trigger sensor that accepts the galactosyltransferase, which is bio trigger material of a spermatozoon.

DETAILED DESCRIPTION OF THE PREFERRED EMBODIMENT

Hereinafter, a detailed description will be given with reference to the attached drawings as to preferred embodiments of the present invention.

First, an explanation will be given with reference to FIG. 1 and FIG. 2 as to the composition of an automatic bio-manipulation factory system for manipulating a single cell according to a preferred embodiment of the present invention.

Figure 1:
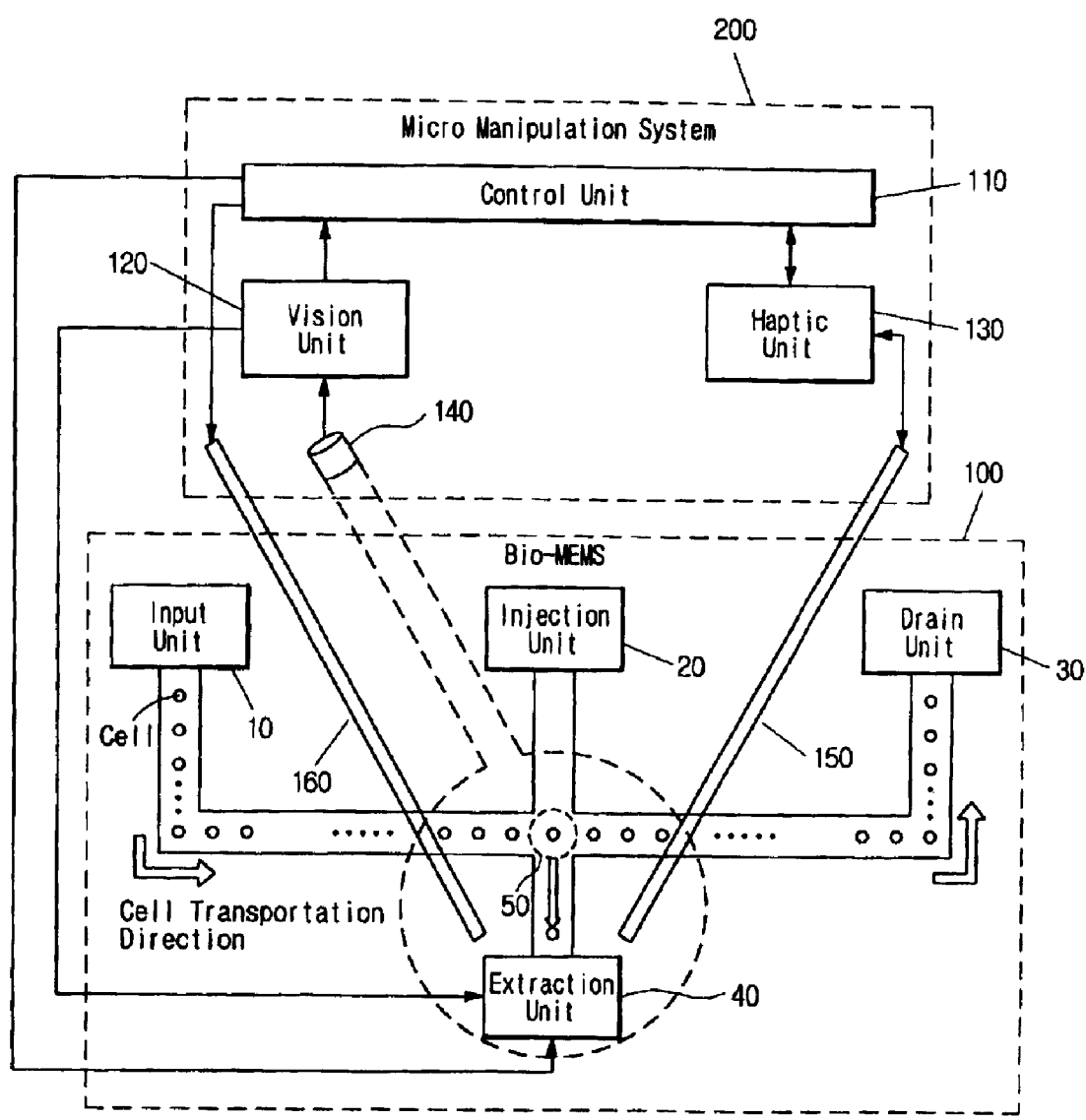
FIG. 1 is a diagram that illustrates a preferred embodiment of the automatic bio-manipulation factory system for manipulating a single cell.
Figure 2:
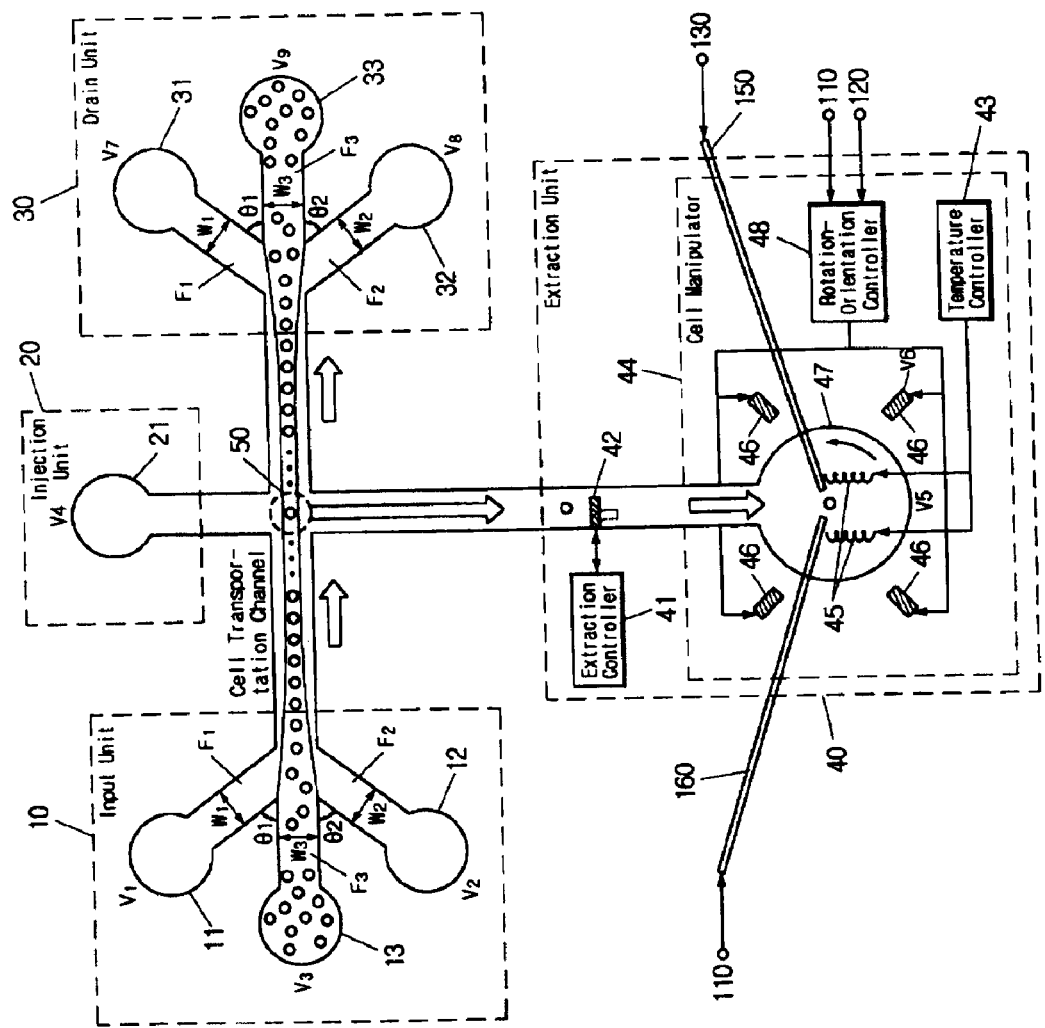
FIG. 2 is a block diagram that illustrates the bio-MEMS in the present invention shown in FIG. 1.

FIG. 1 is a diagram that illustrates an automatic bio-manipulation factory system for manipulating a single cell and FIG. 2 is a block diagram that illustrates the bio-MEMS in the present invention shown in FIG. 1.

As shown in FIG. 1, the automatic bio-manipulation factory system for manipulating a single cell according to a preferred embodiment of the present invention comprises a bio-MEMS(100) and a micro manipulation system(200).

Preferably, the bio-MEMS(100) transports, separates, and extracts a single cell which will be the subject of the manipulation from a plurality of cells, and controls the rotation-orientation of the cell automatically and maintains the cell temperature to be constant at a certain temperature.

Specifically, the bio-MEMS(100) transports, separates and extracts a single cell to be subjected to the manipulation out of a plurality of cells by using the capillary electrophoresis and a conductive polymer, controls the rotation-orientation of the cell automatically by using the dielectrophoresis, and rotation-orientation feedback information and the cell manipulation order of the operator transmitted by a vision unit(120) in the micro manipulation system(200), and increases the survival rate of the extracted cell during the cell manipulation by using a temperature controller(43).

Further, the micro manipulation system(200) obtains vision information and manipulation information of the extracted single cell and manipulation tool from the bio- MEMS(100) and provides it to the operator. The micro manipulation system(200) also manipulates the extracted single cell by transmitting the rotation-orientation feedback information and the cell manipulation order of the operator to the bio-MEMS(100), and manipulates the manipulation tool by transmitting the tool manipulation order of the operator to the manipulation tool.

Specifically, the micro manipulation system(200) obtains vision information and manipulation information including tactile information about the extracted single cell and the manipulation tool from the bio-MEMS(100) by using the vision unit(120) and the haptic unit(130) and provides such information to the operator. The micro manipulation system (200) also manipulates the extracted single cell by transmitting the rotation-orientation feedback information of the haptic unit(120) and the cell manipulation order of the operator to the bio-MEMS(100) and manipulates the manipulation tool by transmitting the tool manipulation order of the operator to the manipulation tool by using the control unit(110) and the haptic unit(130). Preferably, the manipulation tool means the biomimic smart micro pipette (150) and the holding pipette(160), etc.

First, an explanation will be given with reference to FIG. 1 and FIG. 2 as to the composition of the bio-MEMS(100).

The bio-MEMS(100) comprises an input unit(10), an injection unit(20), a drain unit(30) and an extraction unit (40). The input unit(10) stores a plurality of inputted cells, controls the size of the cell transportation channel by using the capillary electrophoresis caused by the application of the transportation voltage(V3) and the focus voltages(V1,V2), and thereby transports the plurality of cells in one line. The injection unit(20) has an injection port(21) which separates cells to be subjected to the manipulation out of the plurality of cells transported in one line by applying the separation voltage(V4). The extraction unit(40) extracts one cell out of the separated cells by applying the extraction voltage(V5) and then manipulates the rotation-orientation of the cell by applying the rotation-orientation voltage(V6). The drain unit(30) absorbs the rest of the cells other than the cells separated for the manipulation.

Preferably, the input unit(10) comprises a first focus port(11), a second focus port(12) and an input cell storage port(13). The first focus port(11) transports the first flow(F1) by applying the first focus voltage(V1). The second focus port(12) transports the second flow(F2) by applying the second focus voltage(V2) which is the same as the first focus voltage(V1). The input cell storage port(13) stores a plurality of inputted cells and transports the plurality of cells though the third flow(F3) by applying the transportation voltage(V3) to the cell transportation channel formed between the first flow(F1) and the second flow(F2).

The extraction unit(40) comprises an extraction controller (41), a conductive polymer(42) and a cell manipulator(44). The conductive polymer(42) extracts only one cell out of the separated cells. The extraction controller(41) controls the cell extraction conducted by the conductive polymer(42). The cell manipulator(44) controls the temperature of the extracted single cell and the rotation-orientation of the extracted single cell by applying the rotation-orientation voltage(V6).

The cell manipulator(44) comprises a temperature controller(43), a heater(45), rotation-orientation electrodes (46), a rotation-orientation controller(48) and an extraction port(47). The extraction port(47) absorbs the extracted single cell to be subjected to the manipulation by applying the extraction voltage(V5). The heater(45), which is included in the extraction port(47), manipulates the temperature of the extracted single cell (for example, the body temperature of a human). The temperature controller(43) controls the manipulation of the cell temperature manipulated by the heater(45). The rotation-orientation electrodes (46), which are located around the extraction port(47), manipulate the rotation-orientation of the extracted single cell by using the dielectrophoresis caused by the application of the rotation-orientation voltage(V6). The rotation-orientation controller(48) receives the rotation-orientation feedback information and the cell manipulation order of the operator and then controls the cell rotation-orientation manipulated by the rotation-orientation electrodes(46) using such information.

The drain unit(30) comprises a third focus port(31), a fourth focus port(32) and a drain cell storage port(33). The third focus port(31) absorbs the first flow(F1) by applying the third focus voltage(V3). The fourth focus port(32) absorbs the second flow(F2) by applying the fourth focus voltage(V4) which is the same as the third focus voltage (V3). The drain cell storage port(33) absorbs the rest of the cells other than the separated cells to be subjected to the manipulation through the third flow(F3) from the cell transportation channel formed between the first flow(F1) and the second flow(F2) and stores them by applying the drain voltage(V9). In other words, the drain unit(30) has the structure that is symmetric to the structure of the input unit(10).

Next, an explanation will be given with reference to FIG. 1 as to the composition of the micro manipulation system (200).

The micro manipulation system(200) comprises a control unit(110), a vision unit(120), a haptic unit(130), a biomimic smart micro pipette(150) and a holding pipette(160). The vision unit(120) monitors the cell to be subjected to the manipulation and the manipulation tool in real-time by using a fluorescence microscope(140) and then outputs vision information and rotation-orientation feedback information. The haptic unit(130), which includes a force sensor measuring changes in the cell manipulation force, collects and outputs the manipulation information of the cell to be subjected to the manipulation and the manipulation tool, and receives the tool manipulation order of the operator and then outputs it to the manipulation tool. The control unit(110) receives the outputted vision information and manipulation information and provides it to the operator, outputs the cell manipulation order of the operator to the extraction unit(40), and outputs the tool manipulation order of the operator to the haptic unit(130). The biomimic smart micro pipette(150) senses the cell manipulation force, outputs trigger information, and manipulates the cell according to the tool manipulation order of the operator. The holding pipette(160) controls rotation-orientation of the cell when the cell is manipulated and later fixes the orientation of the cell according to the tool manipulation order of the operator transmitted from the control unit(110). Preferably, the microscope(140) is a confocal microscope or an optical microscope.

Hereinafter, an explanation will be given with reference to FIG. 3 as to the composition of the biomimic smart micro pipette(150).

Figure 3:
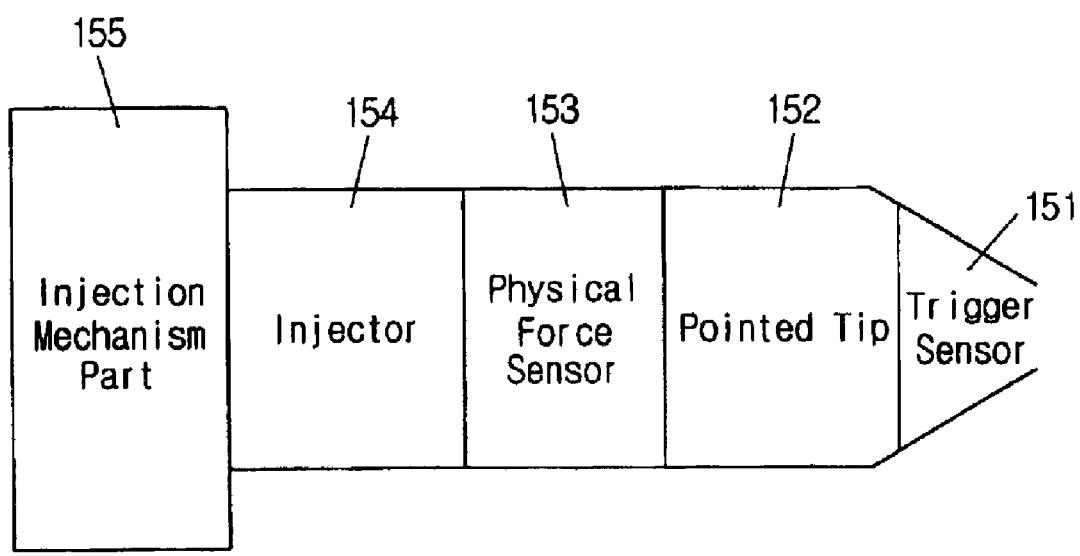
FIG. 3 is a diagram that illustrates the biomimic smart micro pipette in the present invention shown in FIG. 1.
Figure 4A:
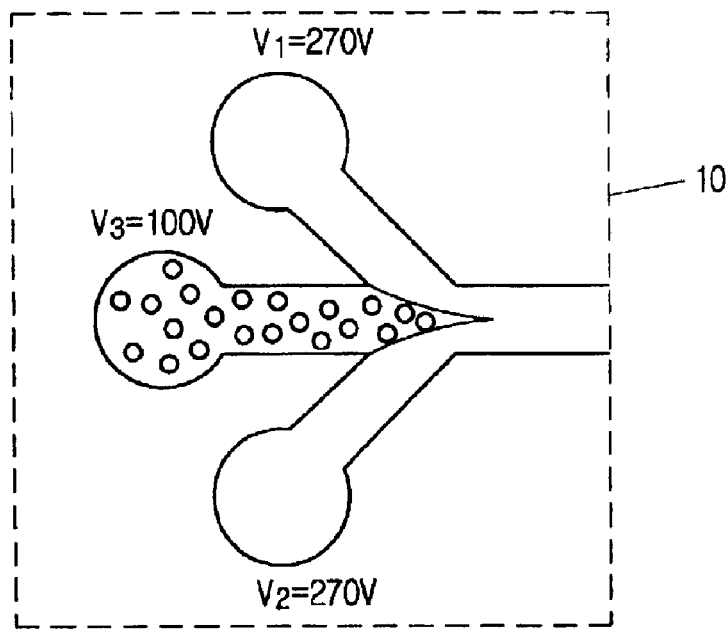
FIG. 4a is a diagram that illustrates the simulation of capillary electrophoresis when the transportation voltage (V3) is 100V.
Figure 4B:
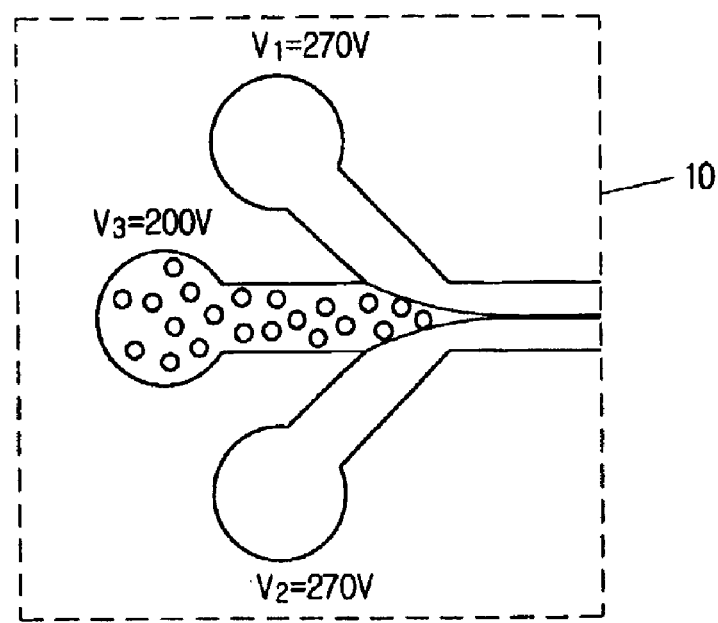
FIG. 4b is a diagram that illustrates the simulation of capillary electrophoresis when the transportation voltage (V3) is 200V.
Figure 4C:
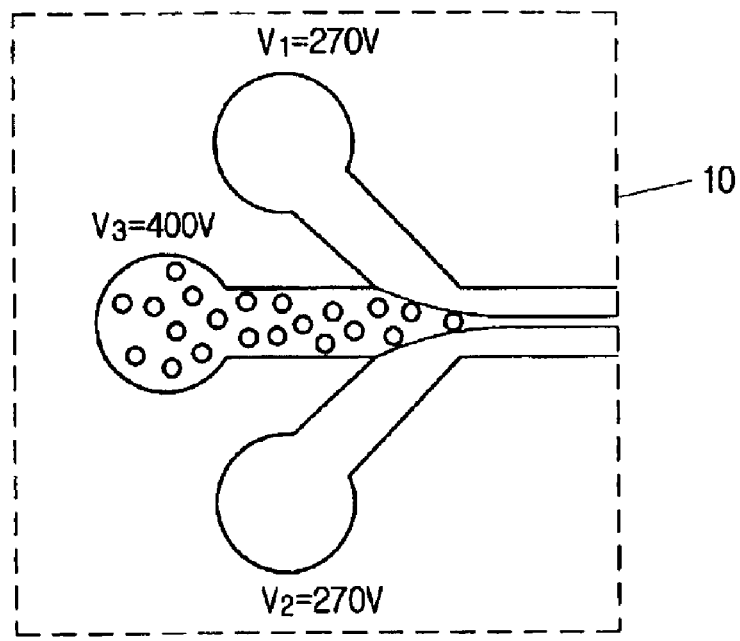
FIG. 4c is a diagram that illustrates the simulation of capillary electrophoresis when the transportation voltage (V3) is 300V.
Figure 4D:
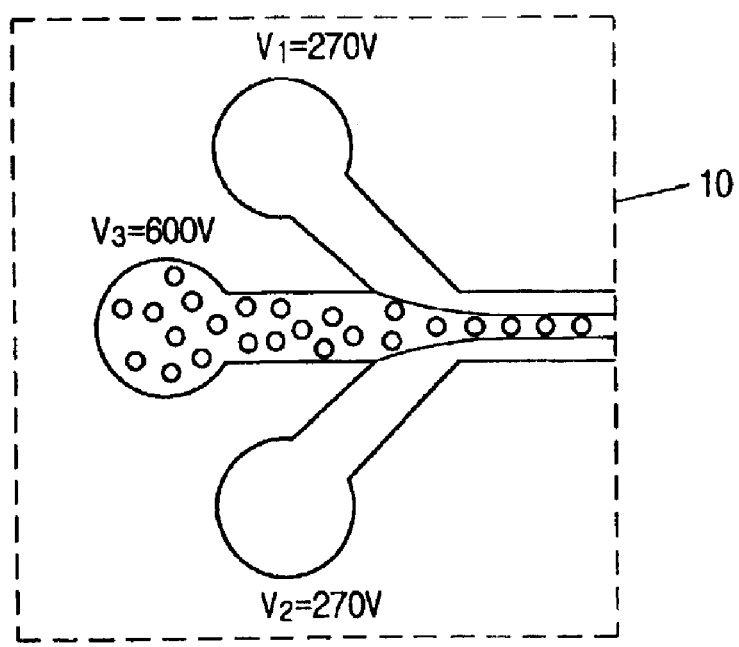
FIG. 4d is a diagram that illustrates the simulation of capillary electrophoresis when the transportation voltage (V3) is 400V.

FIG. 3 is a diagram that illustrates the biomimic smart micro pipette in the present invention shown in FIG. 1.

The biomimic smart micro pipette(150), which is a manipulation tool manufactured to imitate the process of a spermatozoon's invasion into an egg cell, comprises a physical force sensor(153), a trigger sensor(151), a pointed tip(152), an injection mechanism part(155) and an injector (154). The physical force sensor(153) senses the manipulation force at the time of manipulating the cell. The trigger sensor(151) outputs trigger information at the time of contacting the cell. The pointed tip(152) vents chemical material (pH 2)(Acrosomal) which may melt zonapellucida of the cell when a trigger signal generated by the contact of the cell. The injection mechanism part(155) enables precise manipulation at the time of manipulating the cell, while imposing the minimum invasion into the cell through rotation and impact drive mechanism. The injector(154) enables the injection of chemical material or bio-material necessary for the cell manipulation. Preferably, an electric trigger sensor and a bio trigger sensor may be adopted for the trigger sensor(151). The electric trigger sensor outputs the trigger signal by the change in the potential difference of the cell surface and the bio trigger sensor accommodates the galactosyltransferase, which is bio trigger material of a spermatozoon.

Hereinafter, the operation of the automatic bio-manipulation factory system for manipulating a single cell according to a preferred embodiment of the present invention having the above-explained composition will be explained.

First, a operator inputs and stores a plurality of cells into the input cell storage port(13) of the input unit(10) in the bio-MEMS(100) by using the biomimic smart micro pipette (150).

Then, the transportation voltage(V3) is applied to the input cell storage port(13), the first focus voltage(V1) to the first focus port(11) and the second focus voltage(V2) to the second focus port(12). Also, simultaneously, the drain is voltage(V9) is applied to the drain cell storage port(33) of the drain unit(30), the third focus voltage(V7) to the third focus port(31), and the fourth focus voltage(V8) to the fourth focus port(32). Thereafter, the input unit(10) controls the size of the cell transportation channel by using capillary electrophoresis caused by the application of the transportation voltage(V3), the drain voltage(V9) and the focus voltages(V1,V2,V7,V8) and then transports the plurality of cells to the junction point(50) through the flow in one line. Preferably, the drain voltage(V9) applied to the drain cell storage port(33) has the opposite polarity to the transportation voltage(V3). The third focus voltage(V7) and the fourth focus voltage(V8) applied to the third focus port(31) and the fourth focus port(32) respectively have the opposite polarity to the first focus voltage(V1) and the second focus voltage (V2).

FIG. 4 is a diagram that illustrates the simulation of the capillary electrophoresis. In the input unit(10) of the bio-MEMS(100) illustrated in FIG. 2, if the first focus voltage (V1) and the second focus voltage(V2) are applied with 270V and if the transportation voltage(V3) is applied with 100V(FIG. 4a) at first and then with 200V(FIG. 4b), 400V (FIG. 4c) and 600V(FIG. 4d), where the width(W3) of the pipe through which the third flow(F3) is transported, the width(W1) of the pipe through which the first flow(F1) is transported and the width(W2) of the pipe through which the second flow(F2) is transported are all 200 μm and where the angle(θ1) between the pipe through which the third flow(F3) is transported and the pipe through which the first flow(F1) is transported, and the angle(θ2) between the pipe through which the third flow(F3) is transported and the pipe through which the second flow(F2) is transported are all 60°, the size of the cell transportation channel formed between the first flow and the second flow becomes larger as the transportation voltage(V3) increases. Accordingly, by gradually adjusting the transportation voltage(V3) from 100V to 600V, the size of the cell transportation channel can be controlled so that the cells may pass the channel in one line.

Then, if the plurality of cells are transported to the junction point(50) by the capillary electrophoresis, the operator monitors the plurality of cells transported in one line by using the fluorescence microscope(140) and selects cells that will be subjected to the manipulation.

That is, the vision unit(120) of the micro manipulation system(200), through the microscope(140), monitors the plurality of cells transported in one line in three dimensions at the real time and provides the operator with the vision information of the plurality of cells through the control unit(110). Then, the operator selects cells to be subjected to the manipulation out of the plurality of cells transported in one line based upon the provided vision information.

In order to separate the cells selected for manipulation from the junction point(50) toward the extraction port(47) of the extraction unit(40), the separation voltage(V4) is applied to the injection port(21) of the injection unit(20) and the extraction voltage(V5) whose polarity is opposite to the separation voltage(V4) is applied to the extraction port(47) and thus the cells selected for the manipulation are separated and transported toward the extraction port(47). On the other hand, the drain cell storage port(33) of the drain unit(30) absorbs and stores the rest of the cells other than the separated cells to be subject to the manipulation.

At this time, the conductive polymer(42) extracts only a single cell among the cells separated for the manipulation according to the control of the extraction controller(41). Then, only the extracted single cell is transported toward the extraction port(47). That is, because the conductive polymer (42) passes only the single cell out of the cells separated for the manipulation, the other cells are not transported to the extraction port(47).

The conductive polymer(42) will be explained hereinafter with reference to FIG. 5a and FIG. 5b.

Figure 5A:
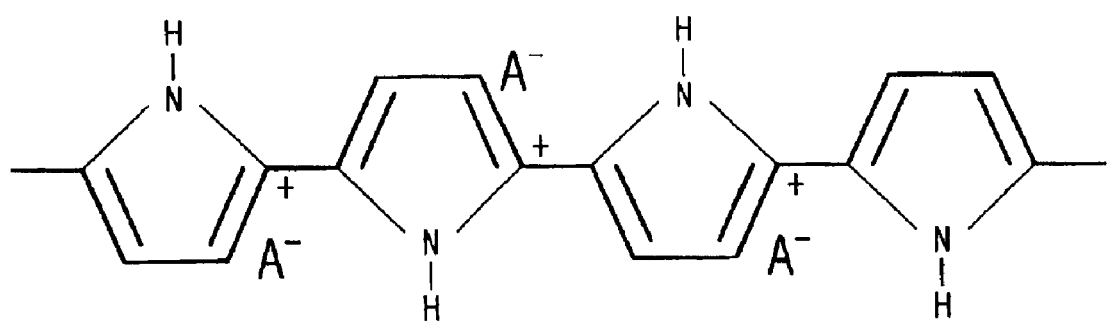
FIG. 5a is a diagram that illustrates the structural formula of a conductive polymer.
Figure 5B:
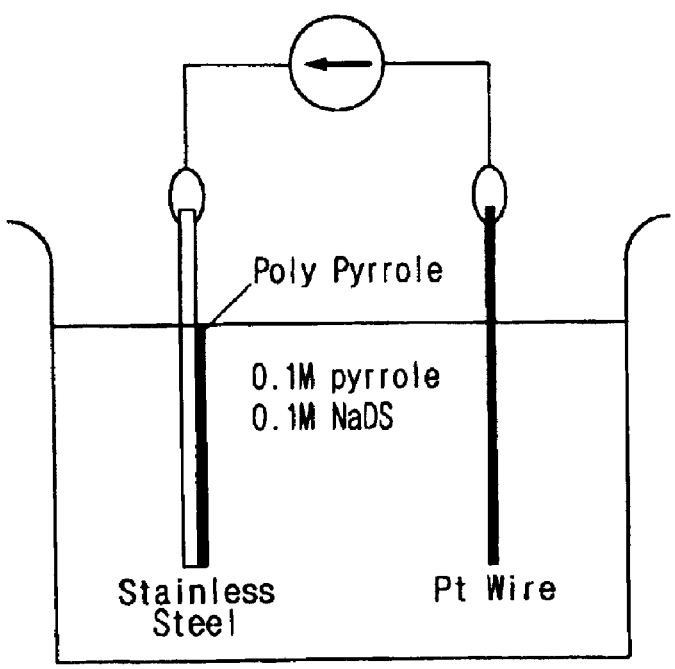
FIG. 5b is a diagram that illustrates the synthetic process of a conductive polymer.

FIG. 5a is a diagram that illustrates the structural formula of the conductive polymer and FIG. 5b is a diagram that illustrates the synthetic process of the conductive polymer.

The conductive polymer(42) is made up of poly pyrrole (PPy) and has the structural formula as illustrated in FIG. 5a. Here, "A" represents a dopant and the bold lines represent backbones. As illustrated in FIG. 5b, for the conductive polymer(42), if constant current is applied to the electrolyte solution(0.1M pyrrole+0.1M NaDs) through stainless steel and Pt wire by using a constant current source, poly pyrrole (PPy) is synthesized on the stainless steel, which is an oxidation-electrode. Because the thickness of the poly pyrrole synthesized in this manner is proportional to the quantity of electric charge provided by the constant current source, the thickness of the conductive polymer(42) can be controlled by adjusting current density and synthesis time.

After the single cell is extracted for the manipulation by the conductive polymer(42), the operator moves the focus orientation of the microscope(140) to the extraction port(47) by manipulating the precision stage.

Hereinafter, an explanation will be given with reference to FIG. 6, FIG. 7 and FIG. 8 as to the concept of a hybrid bio-manipulation system to which the automatic bio-manipulation factory system for manipulating a single cell according to a preferred embodiment of the present invention is applied.

Figure 6:
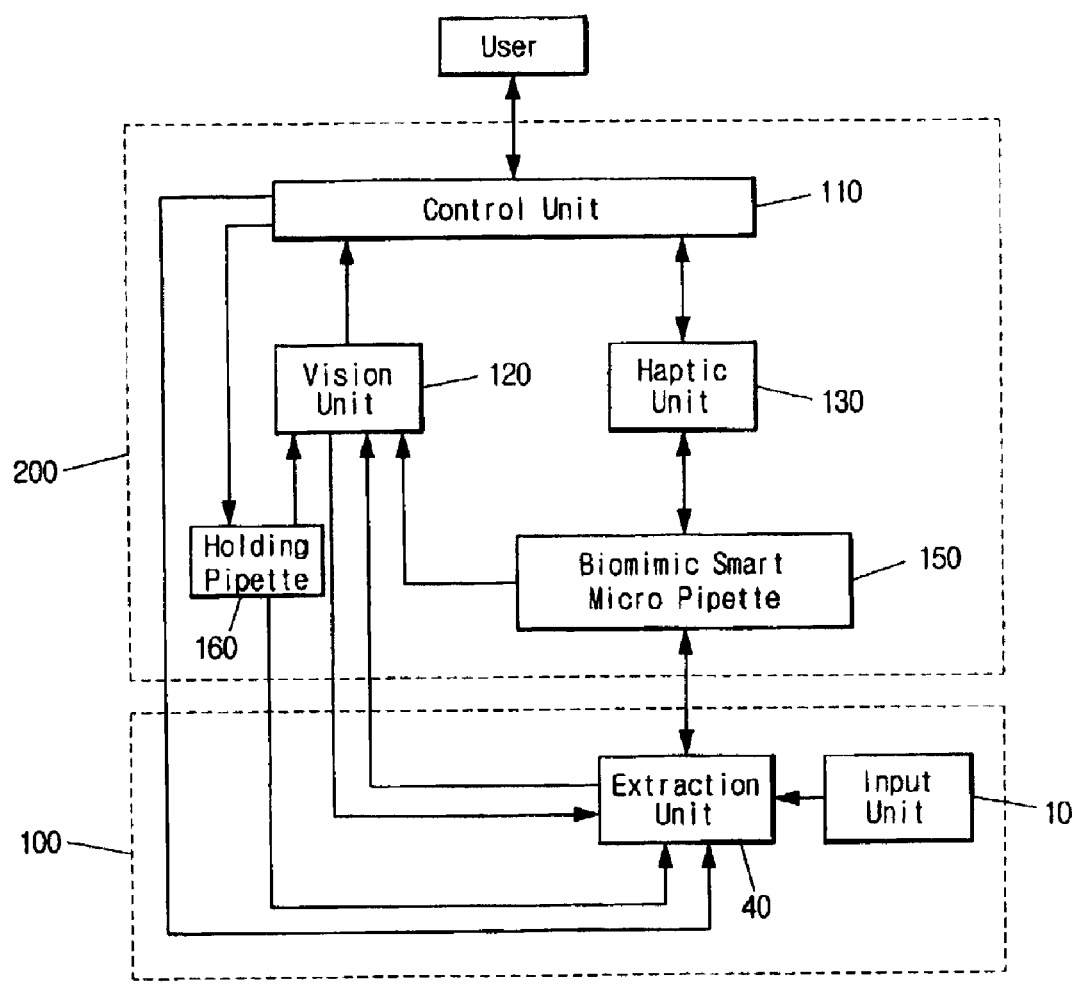
FIG. 6 is a diagram that illustrates the hybrid bio-manipulation system applied to the present invention.
Figure 7:
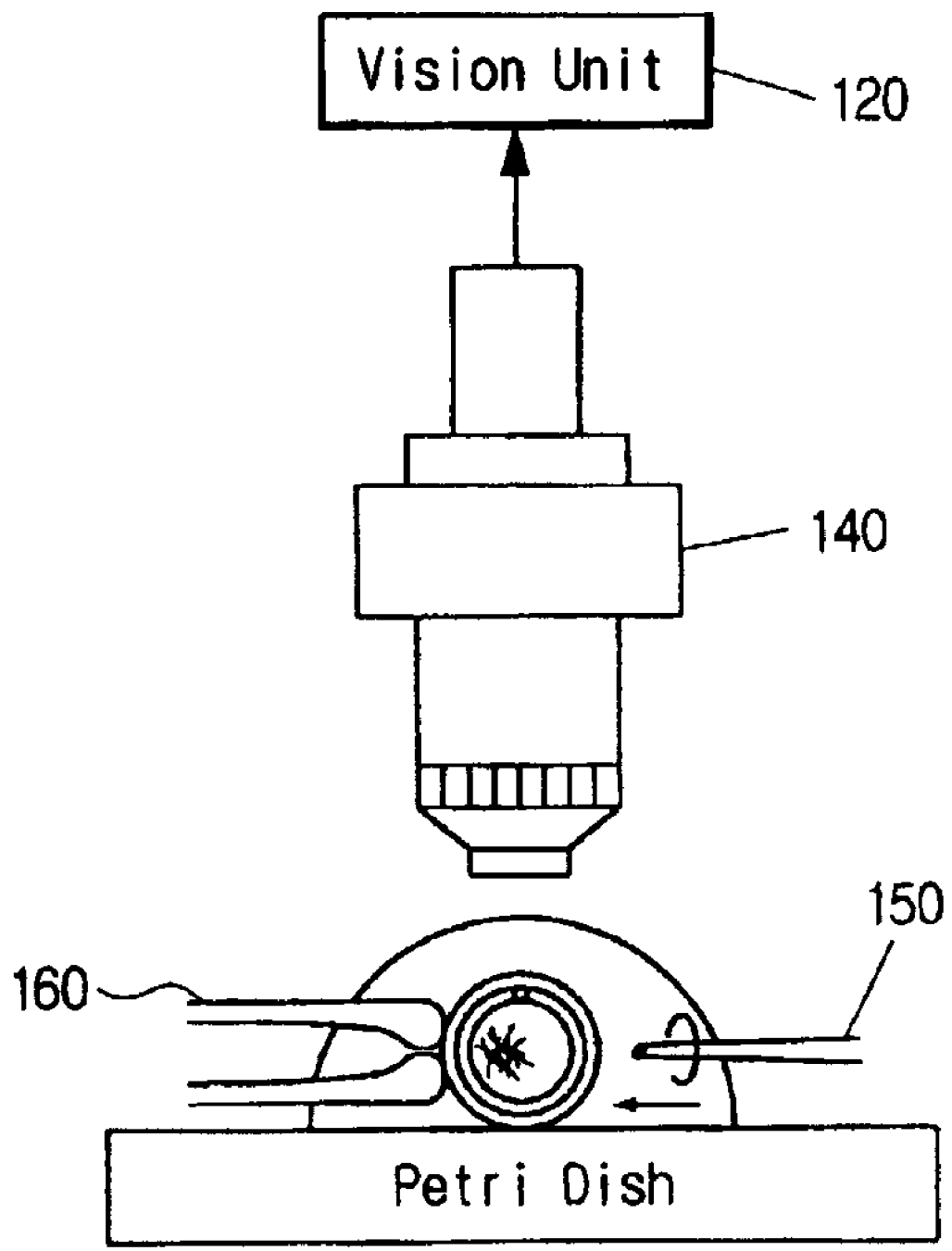
FIG. 7 is a diagram that illustrates a cell manipulation according to the present invention.
Figure 8:
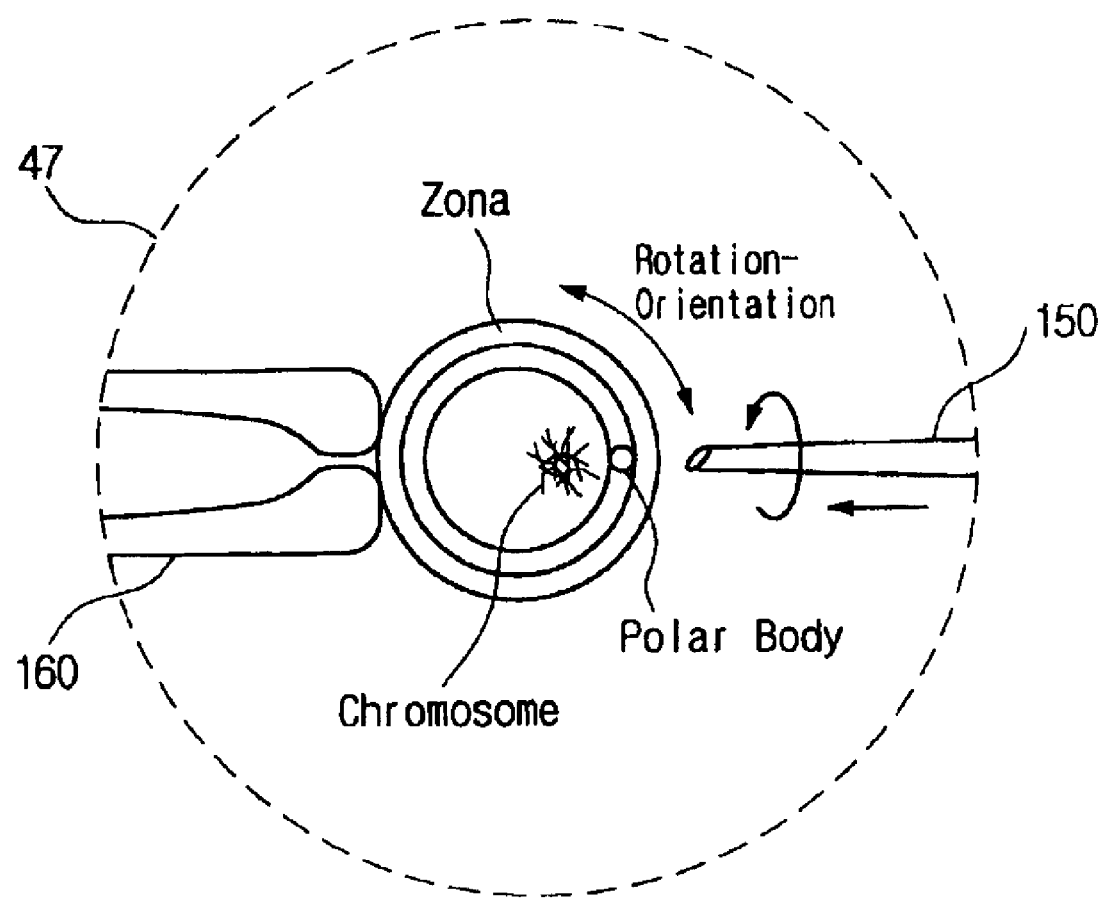
FIG. 8 is a diagram illustrating the magnified view of the cell manipulation illustrated in FIG. 7.

FIG. 6 is a diagram illustrating the operation of a hybrid bio manipulation system applied to the present invention, FIG. 7 is a diagram that illustrates the cell manipulation according to the present invention and FIG. 8 is a magnified view of a cell subject to the manipulation illustrated in FIG. 7.

The hybrid bio-manipulation system according to the present invention makes it possible to precisely manipulate a single cell in a collective and automatic manner by systematically combining the bio-MEMS(100) and the micro manipulation system(200). The operator, while observing the extracted single cell and the manipulation tool (i.e., the biomimic smart micro pipette(150), the holding pipette(160), and etc.) through the microscope(140), manipulates the extracted single cell and the manipulation tool in the bio-MEMS(100) using the micro manipulation system(200).

More specifically, as illustrated in FIG. 6, the vision unit (120) monitors the single cell extracted at the extraction unit(40) of the bio-MEMS(100) and the manipulation tool (i.e., the biomimic smart micro pipette(150), the holding pipette(160), and etc.) in three dimensions and in real-time by using the microscope(140) and acquires the vision information of the extracted single cell and the manipulation tool and then provides such information to the operator through the control unit(110).

The haptic unit(130) collects the manipulation information (i.e., the dynamic and tactile information) of the single cell extracted at the extraction unit(40) of the bio-MEMS (100) and of the manipulation tool by using the biomimic smart micro piepette(150) and provides such manipulation information of the extracted single cell and the manipulation tool to the operator through the control unit(110).

Then, based upon the vision information and the manipulation information, the operator creates manipulation orders for the extracted single cell and the manipulation tool (i.e., cell manipulation order and tool manipulation order) and inputs such orders to the control unit(110). The control unit(110) outputs the inputted cell manipulation order to the cell manipulator(44) in the extraction unit(40) of the bio-MEMS(100) and outputs the inputted tool manipulation order to the biomimic smart micro pipette(150) and the holding pipette(160). The vision unit(120) outputs the rotation-orientation feedback information to the cell manipulator(44).

Accordingly, the cell manipulator(44) receives the cell manipulation order of the operator and the rotation-orientation feedback information of the vision unit(120). The rotation-orientation controller(48) of the cell manipulator(44) controls the rotation-orientation electrode (46) according to the cell manipulation order of the operator and the rotation-orientation feedback information of the vision unit(120). The rotation-orientation electrode(46) manipulates the rotation-orientation of the extracted single cell by using dielectrophoresis caused by the application of the rotation-orientation voltage(V6). Namely, in order for the vision unit(120) to automatically control the rotation-orientation of the cell in accordance with the desired rotation-orientation of the cell or the pre-designated rotation-orientation of the cell through the vision information, the rotation-orientation electrode(46) feedback-controls the orientation of the extracted single cell with the dielectrophoresis caused by the rotation-orientation voltage(V6) (for instance, by the AC voltage of 10 KHz) by using the vision unit(120) and then determines the orientation of the extracted single cell.

The haptic unit(130) provides the operator with the manipulation information in the form of the force feedback through the control unit(110) so that the operator may sense the force caused by the transformation of the cell at the time when the extracted single cell is manipulated by the micro manipulation system(200). Accordingly, it is essential that the haptic unit(130) has the force sensor which can measure the change of force in the biomimic smart micro pipette (150) during the cell manipulation.

Hereinafter, the manipulation of the extracted single cell and the manipulation tool will be explained in detail with reference to FIG. 7 and FIG. 8. As illustrated in FIG. 7 and FIG. 8, the extracted single cell is subject to the rotation-orientation control by the operator or the vision unit(120), and the biomimic smart micro pipette(150) and the holding pipette(160) are subject to the manipulation control by the operator. That is, when the biomimic smart micro pipette (150) manipulates the extracted single cell at the extraction port(47) of the cell manipulator(44) within the extraction unit(40), the haptic unit(130) senses the cell manipulation force through the force sensor and thus acquires the manipulation information. The haptic unit(130) then provides the operator with the acquired manipulation information through the control unit(110). Simultaneously, the vision unit(110) monitors the cell manipulation through the microscope(140) and thus acquires the vision information, and then provides the operator with the acquired vision information through the control unit(110).

Then, the operator transfers the tool manipulation order to the haptic unit(130) and the holding pipette(160) through the control unit(110) and then, if the haptic unit(130) transfers the tool manipulation order to the biomimic smart micro pipette(150), the biomimic smart micro pipette(150) manipulates the extracted single cell at the extraction port (47) according to the tool manipulation order of the operator. The holding pipette(160) controls the rotation-orientation of the extracted single cell and then thoroughly fixes the orientation of the cell according to the tool manipulation order of the operator transferred from the control unit(110).

When the operator transfers the cell manipulation order to the extraction port(47) through the control unit(110), the rotation-orientation controller(48) of the extraction port(47) applies the rotation-orientation voltage(V6) to the rotation-orientation electrodes(46) and controls the rotation-orientation of the extracted single cell according to the cell manipulation order of the operator.

Also, when the vision unit(120) transfers the rotation-orientation feedback information based on the vision information acquired from monitoring by the microscope(140) to the extracted port(47), the rotation-orientation controller(48) of the extraction port(47) applies the rotation-orientation voltage(V6) to the rotation-orientation electrodes(46) according to the rotation-orientation feedback information of the vision unit(120) and thus controls the rotation-orientation of the extracted single cell. Accordingly, the rotation-orientation of the cell may be controlled accurately and automatically according to the operator's desired rotation-orientation or the previously inputted rotation-orientation.

The heater(45) equipped in the extraction port(47) increases the survival rate of the cell during the manipulation by maintaining a certain constant temperature.

The above description of the present invention is intended to be illustrative, but not to limit the scope of the claim. Many alternatives, modifications and variations of the present invention can be embodied to the extent apparent to those skilled in the art.

EFFECT OF THE INVENTION

As described above, according to the present invention which implements a bio-MEMS, it is possible to transport, separate and extract a single cell for manipulation from a plurality of cells, to control automatically the rotation-orientation of the cell, and to increase the survival rate of the cell by controlling the temperature during the cell manipulation. Furthermore, by automating and manipulating the extracted single cell and the tools with a micro manipulation system, the present invention makes it possible to manipulate the cell exactly in the precise orientation of the cell and thus even a non-expert can manipulate the cell accurately. Also, through the present invention, the conventional manual and individualized single cell manipulation can be automated and processed collectively by systematically combining the bio-MEMS with the micro manipulation system.

What is claimed is:

1. An automatic bio-manipulation factory system for manipulating a single cell comprising:
   a bio-MEMS (Micro-Electra Mechanical System) that transports, separates and extracts a single cell for manipulation from a plurality of cells, said bio-MEMS comprises:
      an input unit that stores a plurality of inputted cells and transports the plurality of cells in a line by controlling the size of a cell transportation channel through the use of capillary electrophoresis caused by the application of a transportation voltage and a focus voltage;
      an injection unit including an injection port that separates cells for manipulation from the plurality of cells transported in a line by applying a separation voltage;
      an extraction unit that extracts one of the cells separated for manipulation by applying an extraction voltage and manipulates the rotation-orientation of the cell by applying a rotation-orientation voltage; and
      a drain unit that absorbs the remaining cells other that the cells separated for manipulation; and
   a micro manipulation system comprising:
      an inverted optical microscope that monitors the single cell in the bio-MEMS;
      a microstage which has a 3-degree of freedom to position the bio-MEMS in focus of the optical microscope; and
      an injection pipette for manipulation of the single cell.

2. The automatic bio-manipulation factory system for manipulating a single cell of claim 1, wherein the input unit comprises:
   a first focus port that transports the first flow by applying the first focus voltage;
   a second focus port that transports the second flow by applying the second focus voltage which is the same as the first focus voltage; and
   an input cell storage port that stores a plurality of the inputted cells and transports the plurality of cells though the third flow to the cell transportation channel formed between the first flow and the second flow by applying the transportation voltage.

3. The automatic bio-manipulation factory system for manipulating a single cell of claim 2, wherein the size of the cell transportation channel is such that the plurality of cells may pass in one line.

4. The automatic bio-manipulation factory system for manipulating a single cell of claim 1, the extraction unit comprises:
   a conductive polymer that extracts only one out of the cells separated for manipulation;
   an extraction controller that controls the cell extraction of the conductive polymer, and
   a cell manipulator that controls temperature of the extracted single cell and rotation-orientation of the extracted single cell by applying the rotation-orientation voltage.

5. The automatic bio-manipulation factory system for manipulating a single cell of claim 4, wherein the conductive polymer is made of poly pyrrole.

6. The automatic bio-manipulation factory system for manipulating a single cell of claim 4, wherein the bio-MEMS further comprises:
   an extraction port that absorbs the single cell extracted for manipulation by applying the extraction voltage;
   a heater, included in the extraction port, that manipulates temperatures of the extracted single cell;
   a temperature controller that controls the heater's manipulation of the cell temperature;
   rotation-orientation electrodes, located around the extraction port, that manipulate the rotation-orientation of the extracted single cell using the diclectrophoresis by applying the rotation-orientation voltage, and
   a rotation-orientation controller that receives rotation-orientation feedback information and cell manipulation order of the operator and then controls the rotation-orientation electrodes' manipulation of the cell rotation-orientation.

7. The automatic bio-manipulation factory system for manipulating a single cell of claim 6, wherein the rotation-orientation controller controls automatically the rotation-orientation of the extracted single cell so that it may be located at the operator's desired rotation-orientation or at the previously inputted rotation-orientation according to the rotation-orientation feedback information.

8. The automatic bio-manipulation factory system for manipulating a single cell of claim 1, wherein the drain unit comprises:
   a third focus port that absorbs a first flow by applying a third focus voltage;
   a fourth focus port that absorbs a second flow by applying a fourth focus voltage which is the same as the third focus voltage; and
   a drain cell storage port that stores the rest of the cells other than the cell separated for manipulation through the third flow from the cell transportation channel formed between the first flow and the second flow, by applying the drain voltage.

9. An automatic bio-manipulation factory system for manipulating a single cell comprising:
   a bio-MEMS (Micro-Electro Mechanical System) that transports, separates and extracts a single cell for manipulation from a plurality of cells, said bio-MEMS comprises:
      an input unit that stores a plurality of inputted cells and transports the plurality of cells in a line by controlling the size of a cell transportation channel through the use of capillary electrophoresis caused by the application of a transportation voltage and a focus voltage;
      an injection unit including an injection port that separates cells for manipulation from the plurality of cells transported in a line by applying a separation voltage;
      an extraction unit that extracts one of the cells separated for manipulation by applying an extraction voltage and manipulates the rotation-orientation of the cell by applying a rotation-orientation voltage; and a drain unit that absorbs the remaining cells other that the cells separated for manipulation; and a micro manipulation system comprising:

a vision unit that monitors the extracted single cell and the manipulation tool by using a microscope in real-time and then outputs vision information and rotation-orientation feedback information;

a haptic unit, equipped with a force sensor measuring changes in the cell manipulation force, that collects and outputs information on the extracted single cell and the manipulation tool and that receives tool manipulation order of the operator and then outputs it to the manipulation tool;

a control unit that provides the operator with the outputted vision information and manipulation information, outputs the cell manipulation order of the operator to an extraction unit, and outputs the tool manipulation order of the operator to the haptic unit;

a biomimic smart micro pipette that senses the cell manipulation force, outputs trigger information, and manipulates the cell according to the tool manipulation order of the operator; and a holding pipette that controls the rotation-orientation of a cell at the time of manipulating the cell and then fixes the orientation of the cell according to the tool manipulation order of the operator which has been transmitted from the control unit.

10. The automatic bio-manipulation factory system for manipulating a single cell of claim 9, wherein the microscope, which has the fluorescence function, is a confocal microscope or an optical microscope.

11. The automatic bio-manipulation factory system for manipulating a single cell of claim 9, wherein the vision unit outputs the rotation-orientation feedback information based on the vision information acquired by the microscope's monitoring and controls automatically the rotation-orientation of the extracted single cell so that it may be located at the operator's desired rotation-orientation or at the previously inputted rotation-orientation.

12. The automatic bio-manipulation factory system for manipulating a single cell of claim 9, wherein the biomimic smart micro pipette comprises:

a physical force sensor that senses manipulation force at the time of manipulating the cell;

a trigger sensor that outputs trigger information at the time of contacting the cell;

a pointed tip that vents chemical material which may melt zonapellucida of the cell when a trigger signal is generated by the contact of the cell;

an injection mechanism part that enables accurate manipulation while imposing the minimum invasion on the cell at the time of manipulating the cell by using the rotation and impact drive mechanism; and an injector that enables the injection of chemical material or bio-material necessary for the cell manipulation.

13. The automatic bio-manipulation factory system for manipulating a single cell of claim 12, wherein the trigger sensor is either an electric trigger sensor that outputs the trigger signal by the change in the potential difference of the cell surface or a bio trigger that accepts the galactosyltransferaso, which is bio trigger material of a spermatozoon.

* * * * *